United States Patent [19]

Moulding

[11] 3,993,452
[45] Nov. 23, 1976

[54] DEVICE FOR TIMED REMOVAL AND REPLACEMENT OF A SPECIMEN CONTAINER

[76] Inventor: Thomas S. Moulding, 1954 Glencoe, Denver, Colo. 80220

[22] Filed: July 31, 1975

[21] Appl. No.: 600,645

[52] U.S. Cl. .................................. 23/259; 70/159; 211/4; 211/8; 211/74; 220/23.4; 220/23.86; 346/33 ME
[51] Int. Cl.² .................. B01L 9/00; B01L 11/00; B65D 55/14; E05B 73/00
[58] Field of Search ................ 23/259; 346/33 ME; 211/1.3, 4, 8, 74; 220/23.4, 23.83, 23.86; 116/121, 114 R

[56] References Cited
UNITED STATES PATENTS

| | | |
|---|---|---|
| 3,526,125 | 9/1970 | Gilford et al. ............ 346/33 ME UX |
| 3,786,510 | 1/1974 | Hodges ...................... 346/33 ME |
| 3,826,622 | 7/1974 | Natelson ............................ 23/259 |
| 3,873,273 | 3/1975 | Moran et al. ..................... 23/259 X |

Primary Examiner—Joseph Scovronek
Attorney, Agent, or Firm—Max L. Wymore

[57] ABSTRACT

This apparatus provides a stamp time indication of when a medical or scientific specimen container is made available for use and a second time stamp indication of when the specimen container is rendered unusable, thereby providing a time indication of when the specimen was collected or the specimen container was otherwise utilized.

11 Claims, 9 Drawing Figures

DEVICE FOR TIMED REMOVAL AND REPLACEMENT OF A SPECIMEN CONTAINER

BACKGROUND OF THE INVENTION

In many medical and scientific situations it is extremely important to know when a specimen was collected and/or used. Many times the valuative analysis associated with the use of the specimen will vary with time, and without accurate recognition of the time when the specimen was used the observed results are of limited benefit. For example, in the medical field accurate laboratory tests may involve a series of blood, urine or other specimen collections over a time period. Without recognition of the time in which the specimen was collected laboratory analysis may be impossible because of the incomprehensible and unrelated data. Although the time information may be recorded by the personnel associated with the test, human error often intervenes and results in inaccurately recorded material. Furthermore, in some medical applications the patient himself is required to collect specimens, and this situation is even more prone to result in inaccurately recorded time. Similarly, it is often desirable that a particular specimen be utilized at a particular time so that test data may be collected a predetermined time after use. In order to obtain accurate test data it therefore becomes important to know the time in which the specimen was administered or used. Accordingly, it is an object of this invention to provide an apparatus which accurately records a time period in which a specimen was collected or otherwise used.

It is another object of this invention to provide an apparatus which will eliminate human error in recording the time period at which a specimen was administered or collected.

It is a further object of this invention to provide an apparatus which will greatly aid in the proper analysis of scientific or medical information.

SUMMARY OF THE INVENTION

To achieve these and other objects one form of the invention provides a time clock for registering time indications when a specimen container is removed from a housing that prevents use of the specimen container until the time clock has been activated. The time clock registers the time when the container may first be used and, after the specimen container has been used, the time clock registers the time when the specimen container is returned to a housing that prevents further use of the specimen container. Thus by registering the time during which the specimen container may be first and last used, a time frame is obtained during which the specimen was used or collected, and this time indication is available as recorded data in the analytical process. Since the time registration is an inherent mechanical result of the use of the specimen container, no human error is introduced into the process of recording the time period during which the specimen was used or collected.

BRIEF DESCRIPTION OF THE DRAWINGS

A more complete understanding of the invention may be had by referring to the accompanying detailed description of the invention and drawings in which.

DETAILED DESCRIPTION OF THE INVENTION

Figure 1:
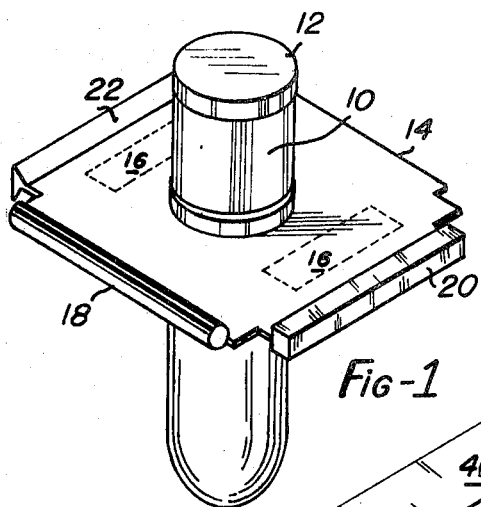
FIG. 1 is a perspective view of a specimen container and a portion of one embodiment of the present invention.

Referring now to FIG. 1, there is shown a specimen container 10 such as a test tube, which may additionally include a cap or stopper 12. A vehicle 14 for supporting the specimen container 10 is also provided, and on the vehicle 14 are time indication or stamp receiving means 16 for receiving a printed time indication. A handle 18 is provided on the vehicle 14 for easily moving the specimen container and the vehicle and to aid in preventing the vehicle from being placed within housing 30 in an improper orientation. Further included on the vehicle 14 are indexed supports 20 and 22. Index support 20 is a square cross-section while that of the support 22 is of a triangular shape. As will be more fully described in FIG. 2, these particular index supports are used for aligning the vehicle 14 within a housing in a particular manner such that the time indications printed on the time stamp receiving means 16 will particularly identify the beginning and end times during which the specimen container was available for use. Although the particular cross-sections of the index supports 20 and 22 are square and triangular respectively, other cross-sections and other index arrangements may be employed, as understood in the art.

Figure 4:
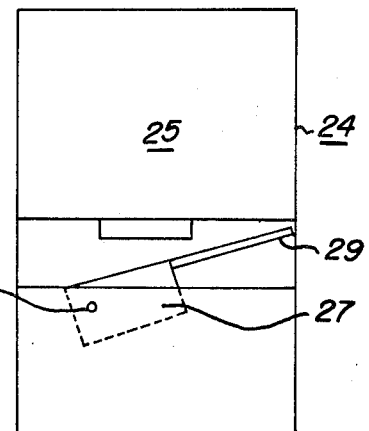
FIG. 4 is an expanded view of a portion of FIGS. 2 and 3.
Figure 2:
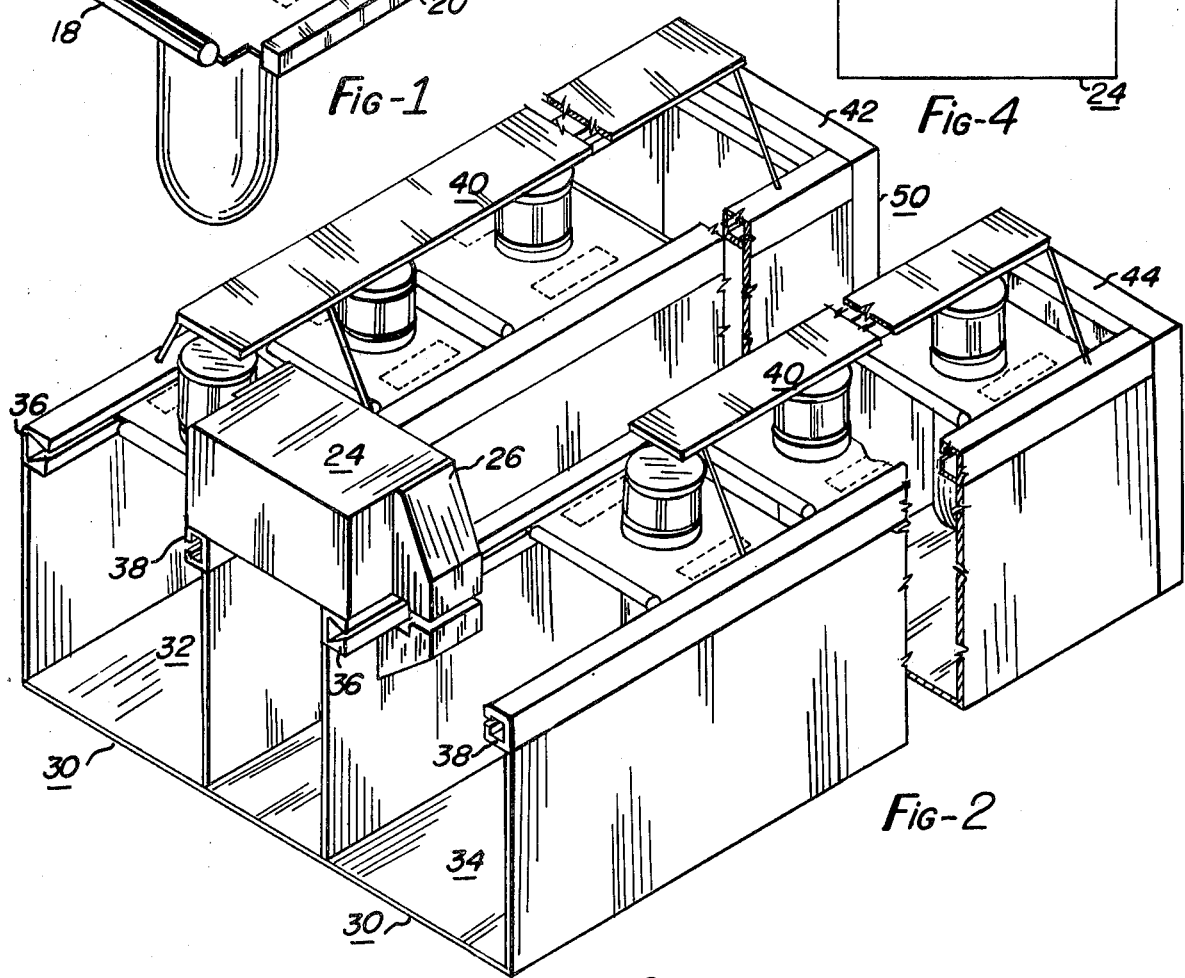
FIG. 2 is a perspective view of one embodiment of the present invention.
Figure 3:
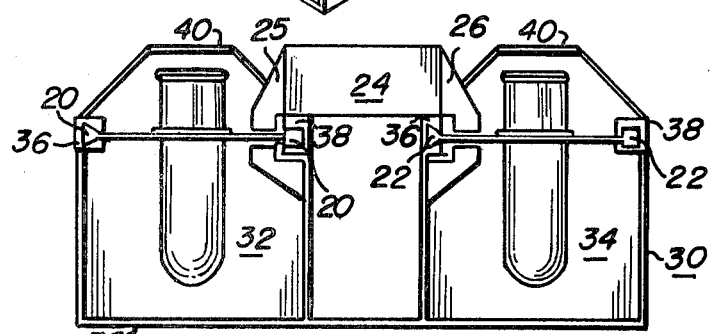
FIG. 3 is an end view of FIG. 2.

Referring now to FIGS. 2, 3 and 4, in which similar elements are designated by similar identification numerals as is the situation with other figures, there is shown one embodiment of a device for timed removal and replacement of a specimen container 10. A time clock 24 or time recording means is provided with two time stamp heads 25 and 26. Each head includes a trip mechanism 27 for activating the time clock and printing or registering an indication of the time when an object is passed under the head. The trip mechanism 27 illustrated in FIG. 4 is arranged to activate the time clock 24 when an object passes from left to right under the time stamp. As the object passes in this direction the trip mechanism 27 rotates clockwise about pivot 28 and triggers time clock 24. Housing 30 is provided for preventing the use of the specimen containers during certain periods of operation as will be discussed more fully subsequently. In the embodiment illustrated in FIGS. 2 and 3, the housing 30 comprises a first portion 32 and a second portion 34. Each portion 32 and 34 is open ended near the portion of the housing 30 adjacent the time clock 24. Rails 36 and 38 are provided within each housing and have internal openings corresponding to the geometric cross-section of the index supports attached to the vehicle 14. Rails 36 and 38 comprise one embodiment of means for movably supporting the vehicle 14 within the portions 32 and 34, while also aligning the vehicle in the appropriate orientation in each portion of the housing with respect to the time clock 24. One-way gates are provided near the open ends of portions 32 and 34. Each one-way gate functions to restrict the movement of the specimen container 10 on rails 36 and 38 so that the vehicle 14 may only be removed from the open end of the first portion 32 and inserted in the open end of the second portion 34. An example of such a one-way gate is shown in FIG. 4 where an extension 29 is attached to trip mechanism 27. The extension prevents passage of the vehicle 14 from right to left under the time stamp but moves out of the way when the vehicle moves under the time stamp in the desired direction. The housing further includes covers 40 which comprise one embodiment of a means for preventing access to the caps 12 of each specimen container 10 so long as each vehicle and container remains within the housing. End plates or doors 42 and 44 are provided for inserting the vehicles holding the specimen containers within the first portion of the housing and for removing the vehicles and specimen container from the second portion of the housing, respectively. The doors 42 and 44 may be locked so as to eliminate access to the vehicles 14 and their associated specimen container 10 except through the open ends of the first and second portions 32 and 34, respectively of the housing. Thus, the described portions of the housing may serve as a means for preventing use of the specimen container other than between the time when the time clock has been activated.

The operation of the embodiment illustrated in FIGS. 2, 3 and 4 is as follows. The vehicles 14 each having a specimen container 10 are inserted through the door 42 into the first portion 32 of the housing 30 at an appropriate time before the specimen is to be collected or used. The door 42 is locked and in conjunction with the cover 40 prevents access to the specimen containers. As many vehicle with their associated specimen containers may be inserted in the first portion 32 of the housing as is necessary for a particular analytical procedure being conducted. At the point when a specimen is to be first collected or used, a person grasps the vehicle 14 by the handle 18 and slides the vehicle toward the open end on the index rails 36 and 38. As the vehicle passes the time stamp head 25 of the clock 24 the trip mechanism 27 is activated and a time indication is registered on the time stamp indicator 16 as the vehicle passes out of the open end of the housing. The time stamp indication thus indicates the beginning of the time period when the container is rendered usable, since the vehicle is free from the housing which previously prevented its use. After the specimen is collected or used, it is returned to the second portion 34 of the housing 30. The one-way gate prevents its reinsertion in the first portion 32 of the housing. The vehicle is supported by the rails 36 and 38 so that as it passes the time stamp head 26 of the clock 24 a second time registration is imprinted on the time stamp indication means 16. The second time indication indicates the end of the time period in which the specimens could have been collected or used. As the vehicle is moved further past the time stamp head 26, the one-way gate, the portion 34, the cover 40 and the locked door 44 prevent access to the specimen container. At a desired time the used specimen containers are retrieved by unlocking the door 44 and removing the vehicles 14 and their associated containers 10.

Thus two time stamps are indicated on the time stamp receiving means 16 on each vehicle 14 associated with a particular specimen container 10, providing a time period during which the specimen was used or collected. From the foregoing description of operation and elements it can be seen that the apparatus provides a mechanical indication of a time period. Since the time indications are mechanically required before use of the specimen container can be obtained, there is no possibility of human error in registering these time periods.

An alternative arrangement of this embodiment would be to construct vehicle 14 in a circular or disclike form and eliminate the indexed supports. Under these circumstances rails 36 and 38 would be more simply constructed with a single slit in each rail to accept vehicle 14. The specimen containers and vehicles would be moved in and out of housing 30 in the same manner as previously described. The advantage of such an arrangement would be to eliminate the index supports and construction of rails 36 and 38, and make it easier for the users to put the vehicles and specimen containers into the device. In addition, since vehicle 14 is a disc-shape, there will almost always be at least a little rotation between the time the specimen container and vehicle are removed from the portion 32 and returned to portion 34. Therefore, except for very occasional instances, the two time indications would not be superimposed on one another.

Figure 5:
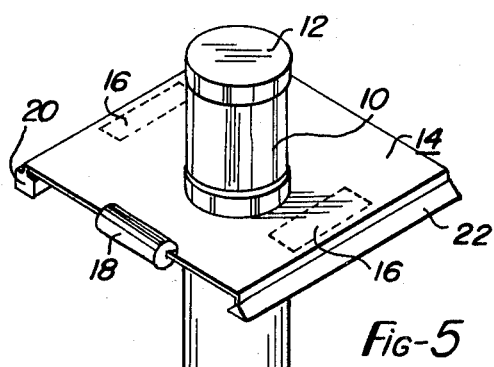
FIG. 5 is a perspective view of a specimen container and a portion of another embodiment of the present invention.

Another form of the vehicle 14 for supporting the specimen container 10 is shown in FIG. 5. In this particular form, the square and triangular shaped cross-section index supports 20 and 22, respectively, protrude downward from the surface of the vehicle 14. This arrangment is necessary for use with the embodiment illustrated in FIGS. 6 and 7, which will now be described.

Figure 7:
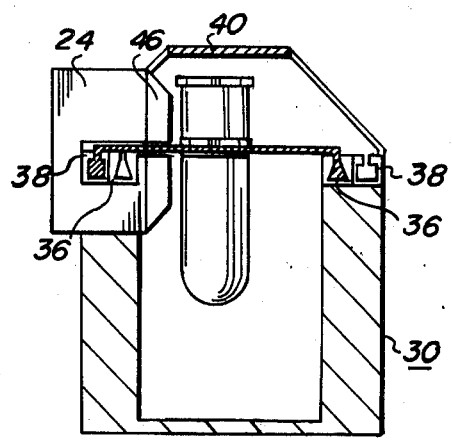
FIG. 7 is an end view of FIG. 6.
Figure 6:
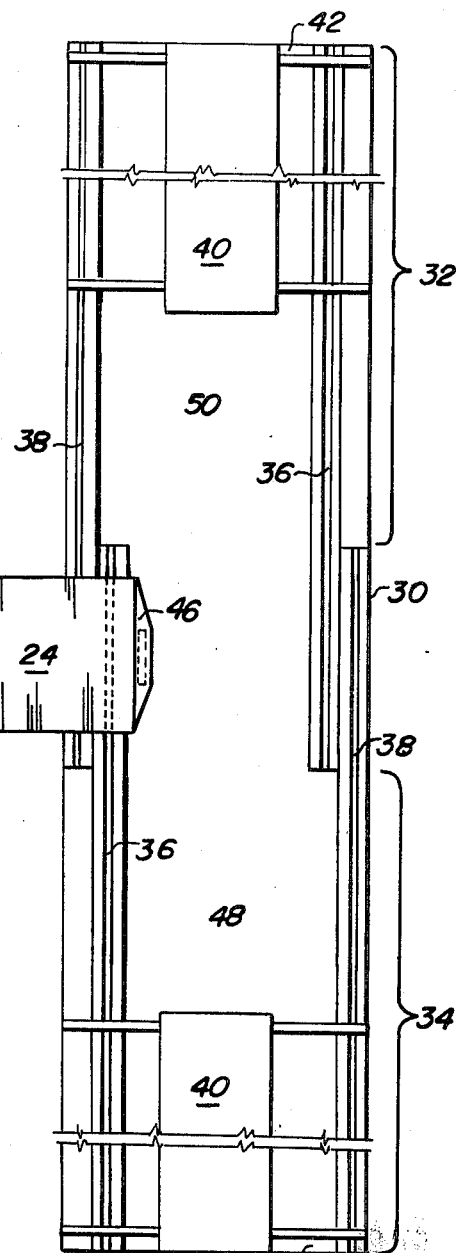
FIG. 6 is a top view of another embodiment of the present invention.

In FIGS. 6 and 7 the first and second portions 32 and 34 of the housing 30 are shown in a substantially aligned position with a time clock 24 intermediate the aligned portions. This embodiment allows a use of a single time stamp head 46. Access openings 48 and 50 are provided on each side of the time clock and the trip actuating mechanism is located relative to both openings. A one-way gate such as that described in FIG. 4 is employed so that vehicles can only be removed from portion 32 and inserted in portion 34.

In operation the vehicles and their associated specimen containers are loaded into the first portion 32 of the housing and are locked therein by the door 42. When it is desired to utilize a specimen the vehicles are moved down the index rails 36 and 38 until the trip actuation mechanism of the time stamp head 46 is encountered. As the vehicle moves past the time stamp head 46, a time indication is registered on the time stamp indicator 16 of the vehicle 14. The vehicle is moved further to the opening 48 where it must be removed due to the termination of the rails protruding from the first portion 32. The vehicle is removed from the access portion 48 and the specimen container may be appropriately used. After the use period the vehicle 14 and its associated container 10 are rotated so the index supports 20 and 22 fit within the index rails 38 and 36, respectively, and the vehicle is inserted into the access opening 50. As the vehicle is moved toward the portion 34 of the housing 30 for receiving the specimen container after it has been used, it encounters the trip mechanism of the clock 24, the time indication from the time stamp head 46 is applied to the time stamp receiving means 16. The vehicle is then caused to move past the access opening 48 to the second portion 34 of the housing 30. After completion of the specimen collection or use process the vehicles and their associated specimen containers may be removed by unlocking the door 44.

Although the time clock 24 described in conjunction with the foregoing two embodiments is automatic in function, it should be understood that a manually operable time clock may be substituted to achieve a portable system. The manual time clock would have to be wound in the convention manner and a manual mechanism used in conjunction with the time stamp head would register the time indication on the time stamp receiving means 16. The manual mechanism for registering the time indication would operate in conjunction with one-way gates in a manner similar to that previously described so that time indications would be manually registered before the vehicle 14 could be removed from the first portion 32 and before the vehicle 14 could be inserted in the second portion 34. The activation of the manual mechanism would not only register a time indication on time receiving means 16, but would also open the one way gates so that specimen container 10 and vehicle 14 could be moved in or out of housing 30.

All of the previous embodiments of this invention require that a card be attached to the specimen container. The use of the card increases the physical dimensions of those devices that have racks for the specimen containers and leads to complexities in construction, loading, etc. In addition, the card attached to the specimen container might make it difficult for a woman to collect a urine specimen and lead to soiling of the card, which would probably reduce patient motivation to cooperate with the collection.

The following is a suggestion for a similar type of device that does not use a card attached to the specimen container. Basically, this device would consist of a first rack or housing for specimen containers before they are removed, and a second rack or housing for specimen containers after they have been removed, filled, or otherwise used and returned to the second rack. There would be a covering on both racks to prevent the specimen container from being opened while in the rack. There would also be a gate on the open ends of both the first and second rack. Wires from this gate would be attached to a device which printed a series of time indications on a card or tape which would move slightly between each printing so that the time indications would not be superimposed on one another.

In operation, a specimen would be removed from the first rack and pass a gate which would initiate an electrical signal that would cause a time indication to be printed on the card or tape. When the specimen container was returned to the second rack, another gate would cause a second time indication to be printed. The gates would be constructed so that specimens could only be removed from the first rack and only introduced into the second rack. In addition, by means of electrical signals and locking mechanisms at the gates, after one specimen container was removed from the first rack, additional specimen containers could not be removed until a specimen container had been placed in the second rack. Similarly, a second specimen container could not be placed in the second rack until an additional specimen container had been removed from the first rack.

To detect the possibility that separate containers could be placed in the second rack that had never been in the first rack, the containers could be specially identified by etching the glass of the container or various types of special marks. To further void confusion, the specimen container could be numbered and placed in sequence in the first rack before the investigation was initiated.

After the specimen containers had been removed from the first rack, used, and placed in the second rack, there would be a series of printed time indications on the tape or card. In reality there would be a series of pairs of time indications. These pairs would represent the time when the various specimen containers had been removed and returned to the rack. To determine which pair of times applied to which specimen container, one would simply have to match the order of the time pairs and the order of the specimen containers that were collected in the second rack.

Figure 8:
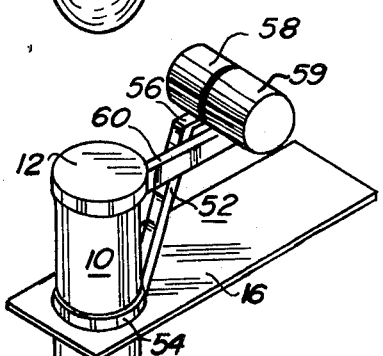
FIG. 8 is a perspective view of a portion of an alternative embodiment of the present invention; and, FIG. 9 is an end view of the remaining portion of the embodiment of the present invention illustrated in FIG. 8.
Figure 9:
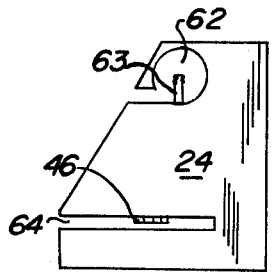

Another embodiment of the present invention is illustrated in FIGS. 8 and 9. Shown in FIG. 8 is the specimen container 10, the cap 12, and a frame 52 for supporting the specimen container 10 and its associated cap. An annular portion 54 of the frame 52 surrounds the specimen container 10 and provides a method by which the time stamp receiving means 16, which in this situation may be a time card, is connected to the frame 52. The annular portion 54 is connected to a locking means or mechanism 58 by an extension 56 of frame 52. The cap 12 is connected by extension 60 to a rotatable portion 59 of the locking mechanism 58. The locking mechanism 58 is a conventional arrangement in which in the unlocked position the extensions 56 and 60 are free to rotate or hinge about the lock mechanism 58. In the locked condition the extensions 56 and 60 are rigidly restrained with cap 12 fastened tightly on specimen container 10.

The remaining portion of the apparatus necessary to provide time indications between which the specimen container 10 is used is illustrated in FIG. 9. Shown there is the time clock 24 having a single time stamp head 46 and a different actuating mechanism. An incorporated additional feature of the time clock 24 in this embodiment is an apparatus or means for changing the condition of the lock mechanism 58 simultaneously with the registering of the time indication on the time card. Such apparatus is illustrated as the receptacle 62 for receiving the locking mechanism 58, key 63 within receptacle 62 for insertion within the locking mechanism 58 to change conditions of the locking mechanism when rotated by channel 64 for receiving the time card 16.

In the operation of this embodiment, the specimen container 10, cap 12, frames 52 and 60, and the time stamp receiving means 16 are initially prepared and the locking mechanism 58 is locked with a separate key having a configuration identical to key 63 thus locking cap 12 on specimen container 10. When it is desired to use the specimen container, locking mechanism 58 is inserted into receptacle 62 and receives key 63 as the time card is inserted into channel 64 to bring it under time stamp head 46. The time clock is activated by turning key 63 to unlock locking mechanism 58 and to cause time stamp head 46 to produce a time indication on card 16. Since cap 12 on the specimen container 10 is rendered freely movable by the unlocking of locking mechanism 58, the specimen container may be used. After use, the specimen container, the frame and time card are returned to the time clock where they are once again inserted and a second time indication is registered as the key 63 is turned to lock the locking mechanism, thus preventing further access to the specimen container 10.

The time clock 24 in the embodiment of FIG. 9 is arranged so that the two time stamp indications do not overlap or obliterate each other. Since key 63 is turned in different directions to lock and unlock the locking mechanism this different turning movement may be used to offset the position of the time indication as registered by the time stamp head 46. Alternatively, two time stamp heads could be provided one for registering the time of unlocking and the other for registering in a different place on the time card the time of locking. It should also be understood that a manual time clock could also be used in this embodiment. In employing a manual time clock a gate mechanism would be operable in conjunction with key 63 and receptacle 62 to prevent removal of the frame 52 from the time clock 24 until the time stamp head was manually caused to register the time indication on the time card.

From the above descriptions of a number of the embodiments of the present invention it can be seen that accurate time indications of when a specimen is used or collected are accurately and reliably obtained without the possibility of intervening human error, and therefore, that the objects of the invention have been achieved. Although a number of embodiments of the device for timed removal and replacement of a specimen container have been shown and described, those skilled in the art will perceive changes and modifications without departing from the invention. For example, it is within the intended scope of this invention to include those applications in which a medication may be dispensed from the specimen container within the time period in which the specimen container is rendered usable. Therefore, it is intended by the appended claims to cover all such changes and modifications as fall within the true spirit and scope of the invention.

We claim:

1. An apparatus for providing time indications between which a specimen container is rendered available for use, comprising:
   time stamp receiving means associated with a specimen container;
   a time recording means for registering time indications on said time stamp receiving means, the time registrations including a beginning time indication when the specimen container is first rendered available for use and an ending time indication when the specimen container is last available for use, said time recording means being operative to register the time indications when actuated;
   means for actuating said time recording means when the specimen container is first rendered available for use and is last available for use, said actuating means operating when said time stamp receiving means is in condition to receive time registrations from the time recording means, said actuating means being operatively connected with said time recording means; and,
   means in conjunction with said actuating means for preventing the use of the specimen container until said actuating means has been operated to first actuate said time recording means and for preventing its use after said actuating means has been operated to last actuate said time recording means.

2. The apparatus as recited in claim 1, further including a vehicle for supporting the specimen container, and wherein:
   the time stamp receiving means is connected to the vehicle;
   the use preventing means comprises a housing including means for movably supporting the vehicle and means for preventing access to the specimen container; and,
   the actuating means comprises an opening in the housing for providing access to the vehicle and a trip mechanism for actuating the time recording means upon movement of the vehicle through the opening.

3. The apparatus as recited in claim 2 wherein the vehicle further includes indexed supports for aligning the vehicle within the housing in one manner before the specimen container is used and in another manner after the specimen container is used.

4. The apparatus as recited in claim 2 wherein the housing further includes lockable means for inserting the specimen containers prior to use and lockable means for retrieving the specimen containers after use.

5. The apparatus recited in claim 3 wherein the housing further comprises a first portion for receiving the vehicle and specimen container before use and a second portion for receiving the vehicle and specimen container after use.

6. The apparatus recited in claim 5 wherein the first and second portions have open ends and the trip mechanism is located adjacent both open ends, whereby the movement of the vehicle through the open end causes the trip mechanism to operate the time recording means to provide a time registration on the time stamp receiving means, the time registration being positioned adjacent to the index supports of the vehicle.

7. The apparatus as recited in claim 5 wherein the first and second portions each have an open end and a locked end; and further including one-way gates located in each portion to restrict movement of the vehicle to a single direction through each open end.

8. The apparatus as recited in claim 5 wherein the first and second portions are aligned with the time recording means intermediate the two portions, and further including an access opening on each side of the time recording means, and the trip mechanism being located adjacent both access openings, whereby vehicle movement in conjunction with the use of an access opening causes the trip mechanism to actuate the time recording means to provide a time registration on the time stamp receiving means, the time stamp receiving means being positioned adjacent the index supports of the vehicle.

9. The apparatus as recited in claim 1 further including a frame for supporting the specimen container, and wherein:
   the time stamp receiving means is connected to the frame;
   the use preventing means comprises a portion of the frame having a lock actuated member for preventing access to the specimen container when locked; and
   the time recording means further including means for changing the condition of the lock member simultaneously with the registering of time indications;

whereby simultaneously with the registration of a time indication on the time stamp receiving means, the means for changing the condition of the lock member changes the condition of the lock member so that the specimen container is first rendered available for use or is no longer available for use.

10. The apparatus as recited in claim 2 wherein the housing includes rails for supporting the vehicle.

11. An apparatus for providing time indications between which a specimen container is rendered available for use, comprising:

time indication receiving means;

time recording means for registering time indications on said time indication receiving means, the time registrations including a beginning time indication when the specimen container is first rendered available for use and an ending time indication when the specimen container is last available for use, said time recording means being operative to register the time indications when actuated;

means for actuating said time recording means when the specimen container is first rendered available for use and is last available for use, said actuating means operating when said time indication receiving means is in condition to receive time registrations from the time recording means, said actuating means being operatively connected with said time recording means; and means in conjunction with said actuating means for preventing use of the specimen container until said actuating means has been operated to first actuate said time recording means and for preventing its use after said actuating means has been operated to last acutate said time recording means.

* * * * *